United States Patent
Tsuji

(10) Patent No.: US 7,110,502 B2
(45) Date of Patent: Sep. 19, 2006

(54) RADIOGRAPHIC APPARATUS AND METHOD FOR SWITCHING A GRID

(75) Inventor: Osamu Tsuji, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/844,982

(22) Filed: May 12, 2004

(65) Prior Publication Data

US 2004/0228439 A1  Nov. 18, 2004

(30) Foreign Application Priority Data

May 12, 2003  (JP) .............................. 2003-133532

(51) Int. Cl.
*H05G 1/58* (2006.01)
(52) U.S. Cl. ...................... 378/116; 378/155
(58) Field of Classification Search ................ 378/114, 378/115, 116, 154, 155
See application file for complete search history.

(56) References Cited

U.S. PATENT DOCUMENTS

| | | | | |
|---|---|---|---|---|
| 4,099,063 A | * | 7/1978 | Pury et al. ................... | 378/148 |
| 5,262,871 A | * | 11/1993 | Wilder et al. ................ | 348/307 |
| 5,768,336 A | * | 6/1998 | Khutoryansky et al. ..... | 378/114 |

| | | | | |
|---|---|---|---|---|
| 2001/0033638 A1 | * | 10/2001 | Inoue ......................... | 378/154 |

FOREIGN PATENT DOCUMENTS

| | | |
|---|---|---|
| JP | 2 -191936 | 7/1990 |
| JP | 3-053238 | 3/1991 |
| JP | 03-289275 | 12/1991 |
| JP | 61-220631 | 5/1994 |
| JP | 2003038481 | 2/2003 |

* cited by examiner

*Primary Examiner*—Edward J. Glick
*Assistant Examiner*—Chih-Cheng Glen Kao
(74) *Attorney, Agent, or Firm*—Morgan & Finnegan L.L.P.

(57) ABSTRACT

This invention provides a radiographic apparatus and method, which can suitably set a grid in radiography or fluoroscopy and execute fluoroscopy or radiography of an object under optimum imaging conditions. The radiographic apparatus includes an X-ray unit (102) which irradiates an object with radiation (X-rays), a two-dimensional detector (106) which detects, through a grid, the radiation which has passed through the object, and a read control unit (107) which acquires an image of the object from the detected X-rays. The apparatus further includes a user interface (113) capable of setting imaging conditions such as an X-ray condition, grid condition, and read condition, a grid switching unit (105) which selects one of a plurality of grids on the basis of the set imaging conditions, and a grid stripe reduction unit (109) which reduces grid stripes generated on the image by the grid.

7 Claims, 7 Drawing Sheets

FIG. 2

|  | X-RAY CONDITION | GRID CONDITION | READ CONDITION |
| --- | --- | --- | --- |
| FLUOROSCOPY | SMALL TUBE CURRENT<br><br>LOW TUBE VOLTAGE | FLUOROSCOPIC GRID<br><br>LOW GRID RATIO<br><br>LOW FREQUENCY | HIGH AMPLIFICATION DEGREE<br><br>LARGE READ PIXEL PITCH |
| RADIOGRAPHY | LARGE TUBE CURRENT<br><br>HIGH TUBE VOLTAGE | RADIOGRAPHIC GRID<br><br>HIGH GRID RATIO<br><br>HIGH FREQUENCY | LOW AMPLIFICATION DEGREE<br><br>SMALL READ PIXEL PITCH |

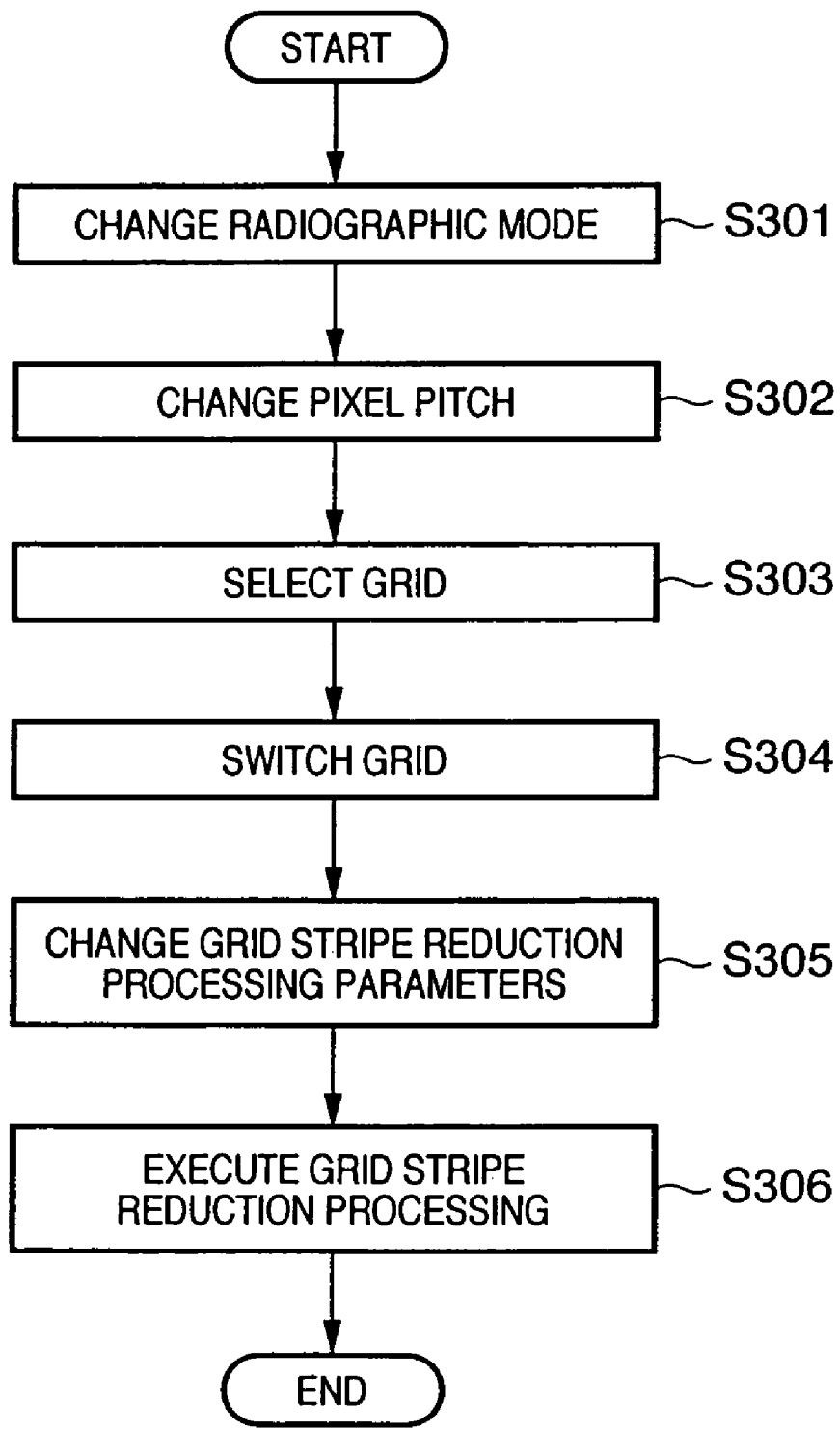

FLUOROSCOPIC GRID    RADIOGRAPHIC GRID

GRID RATIO 4 : 1     GRID RATIO 10 : 1

RADIOGRAPHIC APPARATUS AND METHOD FOR SWITCHING A GRID

FIELD OF THE INVENTION

The present invention relates to a radiographic technique for switching a grid between fluoroscopy and radiography.

BACKGROUND OF THE INVENTION

Conventionally, a grid moving mechanism for a radiographic/fluoroscopic bed (e.g., patent reference 1: Japanese Patent Laid-Open No. 61-220631), a casetteless fluoroscopic/radiographic apparatus (e.g., patent reference 2: Japanese Patent Laid-Open No. 2-191936), and a fluoroscopic/radiographic apparatus (e.g., patent reference 3: Japanese Patent Laid-Open No. 3-53238) are known as techniques using different grids in fluoroscopy (moving image formation) and radiography (still image formation) in a fluoroscopic/radiographic apparatus.

Patent reference 1 discloses a technique related to a reciprocating grid system, that is, a grid moving mechanism for a fluoroscopic/radiographic bed. This system is characterized by comprising a reciprocal reciprocating mechanism capable of transmitting a reciprocation force to a grid incorporated in a snapshot apparatus which executes X-ray imaging, a retracting mechanism capable of retraction driving and loading driving of the grid with respect to the X-ray imaging area, and a connection mechanism capable of connection and disconnection between the grid and the reciprocal reciprocating mechanism. In loading the grid, the connection mechanism connects the grid to the reciprocal reciprocating mechanism. In retracting the grid, the connection mechanism disconnects the grid from the reciprocal reciprocating mechanism.

According to the description in patent reference 1, when divided imaging on one film is to be executed, continuous imaging (rapid imaging) can be performed. In this case, however, when the grid is reciprocated by using the elastic force of a spring, as in a conventional grid mechanism, the reciprocating motion of the grid gradually attenuates with time. For this reason, stripes often remain on the dividedly taken photo in continuous imaging. The stripes cannot completely be removed. Patent reference 1 discloses a grid moving mechanism for a fluoroscopic/radiographic bed, which can prevent any stripe formation on a divisionally taken photo in continuous imaging and retract the grid from the X-ray imaging area when the grid is not used.

Patent reference 2 discloses a casetteless fluoroscopic/radiographic apparatus. This apparatus is characterized by comprising a grid which removes scattering X-rays from an object that is exposed to X-rays from an X-ray source, a detector which is inserted between the grid and a film to detect the X-rays which have passed through the object and output a detection signal to an X-ray controller which controls the X-ray dose, a contact plate which has, on the lower surface, a lead plate that removes backscattering X-rays and with which the film comes into tight contact, a fluoroscopic grid which is arranged in front of an image intensifier that converts the X-rays into an optical image, and removes the scattering X-rays, a mechanism which opens/closes the contact plate to bring the film into tight contact with it, a mechanism which conveys the contact plate brought into contact with the film by the above mechanism from a film transfer position to a radiographic position, fluoroscopic position, and park position and after the end of fluoroscopic/radiographic, returns the contact plate to the film transfer position, and a control mechanism which changes the contact plate to an adapted grid and detector in radiographic and changes the grid to an adapted fluoroscopic grid in fluoroscopic imaging.

According to the description of patent reference 2, to stabilize the density in imaging, the contact plate that is inserted in imaging integrally includes the grid, the film, and the detector (phototimer) to stabilize the density. Patent reference 2 also discloses changing the grid between fluoroscopy and radiography and changing the grid depending on imaging conditions such as the tube voltage even during fluoroscopy.

Patent reference 3 discloses a fluoroscopic/radiographic apparatus which can set a fluoroscopic mode and a radiographic mode. In a steady state, an image intensifier and a fluoroscopic grid are fixed in the X-ray irradiation field. When the radiographic mode is set, an X-ray film contact holder and a radiographic grid are inserted and arranged in the X-ray irradiation field, and the radiographic grid is reciprocated. This apparatus is characterized by comprising a grid fixing frame which fixes the radiographic grid, a grid reciprocating rail which can move the grid fixing frame between a standby position and an imaging position and reciprocate the frame at the imaging position during movement, a holder driving frame to move the X-ray film contact holder between the standby position and the imaging position, and a driving mechanism which moves the holder driving frame to move the X-ray film contact holder. A driven mechanism is arranged between the grid fixing frame and the holder driving frame to make the grid fixing frame follow the holder driving frame and move along the grid reciprocating rail between the standby position and the imaging position when the driving mechanism is driven to move the holder driving frame between the standby position and the imaging position.

The technique described in patent reference 3 aims at making the radiographic grid reciprocating mechanism cooperate with the imaging frame (a structure made by bringing a film and an intensifying screen into tight contact) inserting mechanism. In the embodiment, the fluoroscopic grid is fixed on the overall surface of a fluoroscopic sensor (I.I.)

Under the above-described technical circumstances, a radiographic apparatus can be considered, which selectively uses different grids between fluoroscopy and radiography by using a single FPD (Flat Panel Detector) sensor using a semiconductor.

However, the radiographic apparatus which executes both fluoroscopy and radiography by using the FPD sensor using a semiconductor has the following problems.

(1) The imaging dose in fluoroscopy is about $\frac{1}{100}$ of that in radiography, which is, very small.

(2) In addition to the X-ray dose, the tube voltage also changes between fluoroscopy and radiography. Hence, the grid must appropriately be switched.

(3) When a stationary grid is inserted, moiré is generated in the image depending on the grid frequency and the sampling pitch of the FPD sensor.

(4) If the grid should be reciprocated, the mechanism becomes complex. Hence, setting for obtaining suitable relationships between the image reception frequency and the grid reciprocation period and between the imaging time and the reciprocation speed is also complicated.

SUMMARY OF THE INVENTION

The present invention has been proposed to solve the conventional problems, and has as its objects to provide a radiographic apparatus and method, which can suitably set a grid in radiography or fluoroscopy and execute fluoroscopy or radiography of an object under optimum imaging conditions.

In order to achieve the above object, according to the present invention, there is provided a radiographic apparatus comprising irradiation means for irradiating an object with radiation, detection means for detecting, through a grid, the radiation which has passed through the object, acquisition means for acquiring an image of the object from the detected radiation, setting means for setting imaging conditions, selection means for selecting one of a plurality of grids on the basis of the imaging conditions and grid stripe reduction means for reducing grid stripes generated on the image by the grid.

Furthermore, in order to achieve the above object, according to the present invention, there is provided a radiographic method comprising an irradiation step of irradiating an object with radiation, a detection step of detecting, through a grid, the radiation which has passed through the object, an acquisition step of acquiring an image of the object from the detected radiation, a setting step of setting imaging conditions, a selection step of selecting one of a plurality of grids on the basis of the imaging conditions and a grid stripe reduction step of reducing grid stripes generated on the image by the grid.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 2 is a view showing examples of X-ray, grid, and read conditions in fluoroscopy and radiography;

FIG. 3 is a flowchart for explaining the flow of system control in the radiographic system according to this embodiment;

DETAILED DESCRIPTION OF THE PREFERRED EMBODIMENTS

The embodiments of the present invention will be described below in detail with reference to the accompanying drawings.

<First Embodiment>

Figure 1:
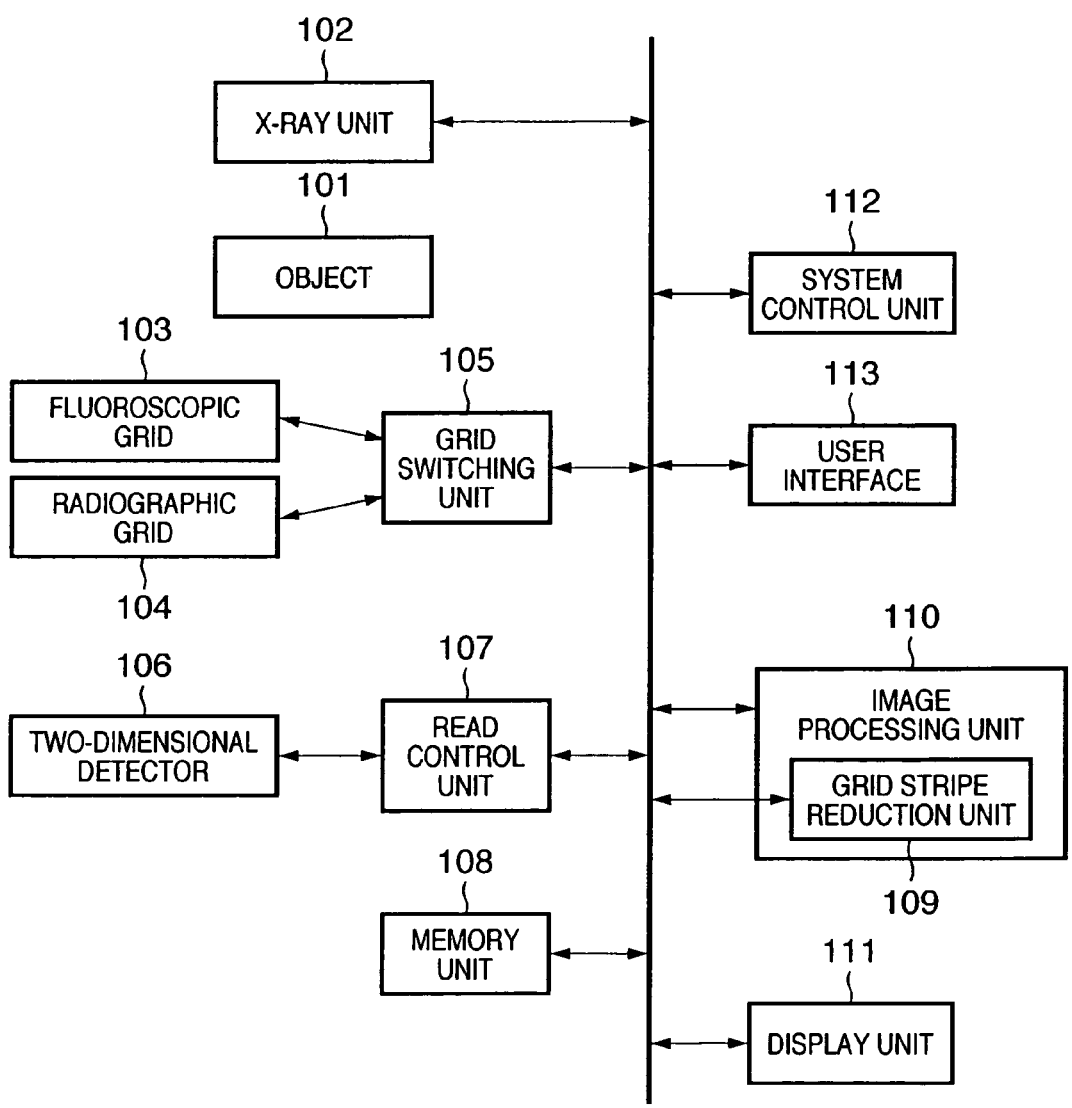
FIG. 1 is a block diagram showing the arrangement of a radiographic system according to the first embodiment of the present invention.

FIG. 1 is a block diagram showing the arrangement of a radiographic system according to the first embodiment of the present invention. As shown in FIG. 1, the radiographic system according to this embodiment includes an X-ray unit 102 which irradiates an object 101 with radiation (X-rays), a grid switching unit 105 which switches between a fluoroscopic grid 103 and a radiographic grid 104, a two-dimensional detection unit 106 which detects the X-rays through a grid, a read control unit 107 which converts the X-rays detected by the two-dimensional detection unit 106 into an optical image (image), a memory unit 108 which stores the image, an image processing unit 110 having a grid stripe reduction unit 109 which reduces grid stripes on the image by the fluoroscopic grid 103 or radiographic grid 104, a display unit 111 which displays the image, a system control unit 112 which controls the respective units, and a user interface unit 113 through which an operator operates/sets the radiographic system.

The system control unit 112 of this embodiment converts items required in fluoroscopy or radiography and decides X-ray, grid, and read conditions. These imaging conditions are not simply divided between fluoroscopy and radiography. The conditions should be classified more finely depending on the imaging part of a patient in fluoroscopy or radiography. In this embodiment, the operator sets a finely classified data acquisition mode (a fluoroscopic mode, a radiographic mode, or a mode with a different degree thereof) by using the user interface unit 113. For this purpose, the user interface unit 113 has a plurality of kinds of imaging buttons to meet detailed requests of the operator for, by example only, the type of the image.

FIG. 2 is a view showing examples of X-ray, grid, and read conditions in fluoroscopy and radiography. In this embodiment, the conditions as shown in FIG. 2 are stored in a memory in the system control unit 112 so that operator's imaging condition setting from the user interface unit 113 can be simplified. More specifically, data related to the X-ray, grid, and read conditions as shown in FIG. 2 are loaded in accordance with the fluoroscopic mode or radiographic mode set through the user interface unit 113 to control the X-ray unit 102, grid switching unit 105, and read control unit 107.

FIG. 3 is a flowchart for explaining the flow of system control in the radiographic system according to this embodiment. As described above, first, the operator sets (changes) the imaging mode through the user interface unit 113 (step S301). Accordingly, the pixel pitch is changed (step S302). More specifically, as shown in FIG. 2, when the fluoroscopic mode is set, the read image pitch is set to "large". When the radiographic mode is set, the read image pitch is set to "small".

More specifically, as a characteristic feature of the radiographic system according to this embodiment, the read control unit 107 changes the read pixel pitch on the basis of the read condition and acquires an image of the object from the X-rays detected by the two-dimensional detector 106.

Next, a grid corresponding to the set mode is selected (step S303). The grid is switched to the fluoroscopic grid 103 or radiographic grid 104 by the grid switching unit 105 (step S304). More specifically, as a characteristic feature of the radiographic system according to this embodiment, the grid switching unit 105 selects the fluoroscopic grid 103 in fluoroscopy of the object and the radiographic grid 104 in imaging of the object.

Figure 4:
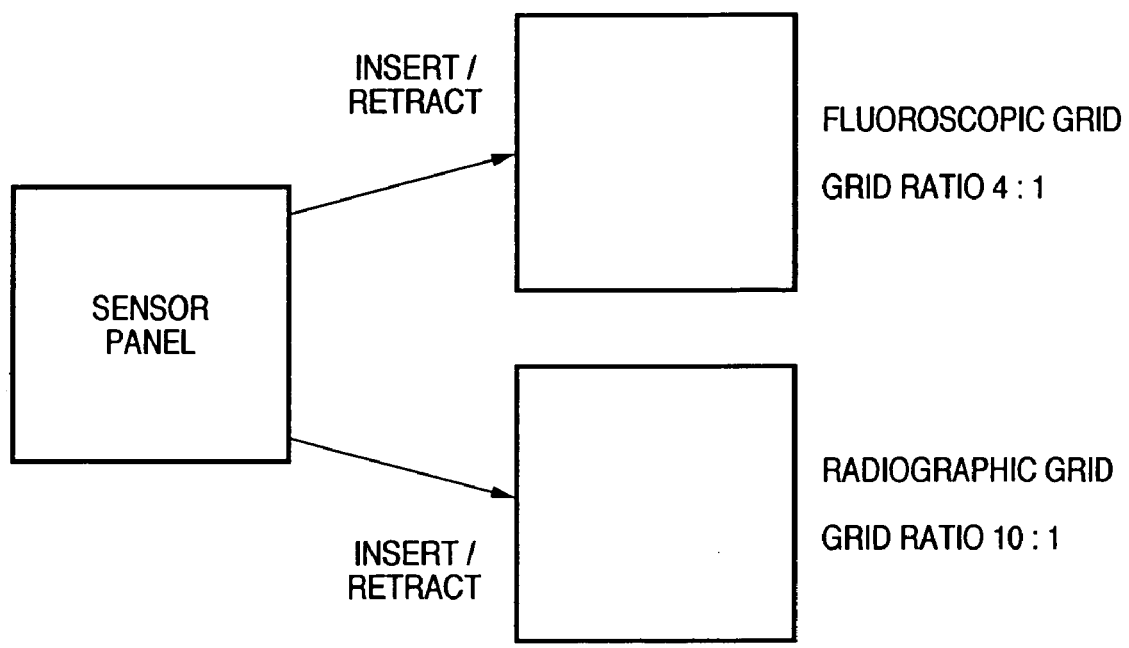
FIG. 4 is a view for explaining grid switching by a grid switching unit 105 according to the first embodiment of the present invention.

FIG. 4 is a view for explaining grid switching by the grid switching unit 105 according to the first embodiment of the present invention. More specifically, in "fluoroscopy", imaging is executed under X-ray conditions with a low voltage and a small current. For this reason, the amount of scattering rays from the object 101 is small. In addition, since the positioning of the object 101 for imaging is important, the spatial resolution and frequency resolution of the acquired image are required to be relatively low. For example, a fluoroscopic grid having a grid ratio of 4:1 is used. On the other hand, in "radiography", the obtained image is used by a doctor for diagnosis. Since an image with a high S/N ratio is required, the tube current becomes large. The tube voltage changes depending on the imaging part of the object (human body). For example, imaging of a chest part is executed using a higher tube voltage than in fluoroscopy or imaging of a abdominal part. In addition, the amount of scattering rays from the object 101 increases depending on the tube voltage or tube current. The pixel value contrast of tissue is required to be high. For these reasons, a grid having a high grid ratio is selected. For example, a radiographic grid having a grid ratio of 10:1 is used.

Figure 5:
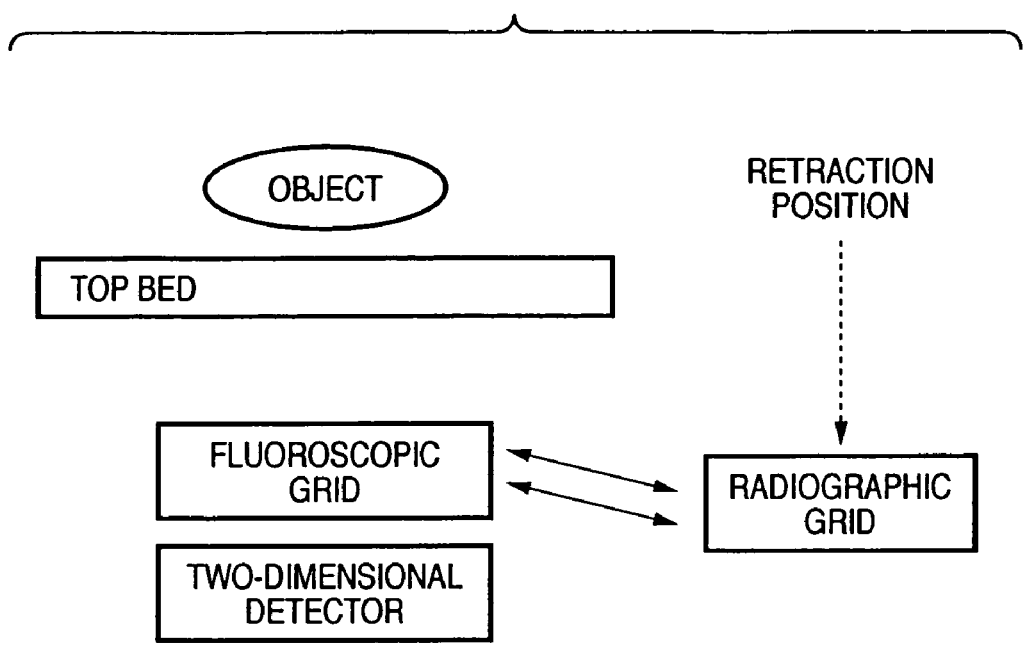
FIG. 5 is a system block diagram for explaining a grid switching state by the grid switching unit 105 according to the first embodiment of the present invention.

FIG. 5 is a system block diagram for explaining a grid switching state by the grid switching unit 105 according to the first embodiment of the present invention. As shown in FIG. 5, the radiographic grid or fluoroscopic grid is inserted between the detector and the object in correspondence with switching of the data acquisition mode. The grid that is not to be used is stopped at the retraction position.

After switching the grid, the object 101 is irradiated with X-rays from the X-ray unit 102 to execute fluoroscopy or radiography, thereby obtaining an image related to the object, as described above. After that, grid stripe reduction processing parameters are changed to cause the grid stripe reduction unit 109 to reduce grid stripes on the image (step S305). The grid stripe reduction unit 109 executes reduction processing for the grid stripes on the image (step S306).

More specifically, as a characteristic feature of the radiographic system according to this embodiment, the system comprises the X-ray unit 102 which irradiates the object with radiation (X-rays), the two-dimensional detector 106 which detects, through a grid, the radiation which has passed through the object, and the read control unit 107 which acquires an image of the object from the detected X-rays, and further comprises the user interface unit 113 capable of setting imaging conditions (e.g., grid condition), the grid switching unit 105 which selects one of a plurality of grids on the basis of the set grid condition, and the grid stripe reduction unit 109 which reduces grid stripes generated on the image by the grid.

As another characteristic feature of the radiographic system, the imaging conditions include an X-ray condition, and the X-ray unit 102 irradiates the object with radiation on the basis of the radiation condition.

As still another characteristic feature of the radiographic system, the imaging conditions include a read condition, and the read control unit 107 acquires the image of the object from the detected radiation on the basis of the read condition.

Grid stripes that are present in an image obtained in the fluoroscopic mode or radiographic mode and grid stripe reduction processing for reducing the grid stripes will be described below.

In this embodiment, the grid is not reciprocated (i.e., a stationary grid system is employed), as described above. This is because a reciprocating system makes the mechanism bulky and generates heat and noise, as described above, and the reciprocation speed must be changed depending on the acquisition period and imaging time in fluoroscopy. When a stationary grid system is employed, these problems can be solved.

The grid stripe reduction processing of this embodiment is not limited to the stationary grid system. Even when a reciprocating grid system is employed, the grid stripe reduction processing to be described below is effective for reducing grid stripes generated in an image by a grid because of mismatch between the reciprocation speed and conditions.

Various methods can be used for the grid stripe reduction processing in this embodiment. For example, grid stripes can be reduced by a low-pass filter using a grid which has a frequency lower than a Nyquist frequency $F_{nq}$ (=$F_s/2$) calculated from an image pitch $F_s$ of a two-dimensional sensor (Japanese Patent No. 2507659). In this method, since the image pitch $F_s$ of a two-dimensional sensor changes between a fluoroscopic image and a radiographic image, the shape of a low-pass filter is simply changed in correspondence with the image pitch $F_s$. However, the usable grid frequency is also changed in accordance with the image pitch $F_s$.

For example, let $F_s$ be the pixel sample pitch in radiography, $F_g$ be the grid frequency usable at this time in the low-pass filter method, and $F_s/2$ be the pixel sample pitch in fluoroscopy. In this case, the grid frequency $F_g$ usable in fluoroscopy must also be halved. More specifically, the grid frequency usable in fluoroscopy must be equal to or lower than the Nyquist frequency in fluoroscopy. When the pixel pitch changes depending on the data acquisition mode, the usable grid frequency changes. Accordingly, the grid frequency in the image also changes. Hence, the stripe reduction processing parameters for grid stripe removal (e.g., the cutoff frequency of the low-pass filter) are changed. That is, as a characteristic feature of the radiographic system according to this embodiment, the fluoroscopic grid 103 and radiographic grid 104 have different grid ratios or different grid frequencies.

As another grid stripe reduction processing method, a stripe structure based on a grid is detected, and grid stripes are removed by predicting the stripe structure. In this case, as disclosed in Japanese Patent Laid-Open No. 2003-38481, a grid with a frequency higher than the Nyquist frequency of the pixel pitch is used, unlike the above-described method using a low-pass filter. The invention disclosed in Japanese Patent Laid-Open No. 2003-38481 is a radiographic image acquisition apparatus having an image sensor which samples the intensity distribution of radiation which has passed through an object and acquires image data. As a characteristic feature, this apparatus has a grid having radiation shielding members periodically laid out to reduce scattering radiation from an object or is configured to be able to selectively use the grid. Let $F_s$ be the sampling spatial frequency of the image sensor, and $F_g$ be the spatial frequency of the grid as the reciprocal of the period of the shade of the radiation shielding members of the grid on the image receiving plane of the image sensor. At this time, the apparatus is configured to satisfy $F_g \approx j \cdot F_s/3$ (j is a positive integer except multiples of 3).

In this case, the grid frequency is selected such that the fundamental frequency of moiré equals its second harmonic. Even in this method, when the pixel pitch changes depending on the data acquisition mode, the usable grid frequency changes, and accordingly, the grid frequency in an image also changes. Hence, the stripe reduction processing parameters for grid stripe removal (e.g., the frequency of moiré searched from an image) are changed.

That is, as a characteristic feature of the radiographic system according to this embodiment, when the read pixel pitch is changed on the basis of the imaging conditions set by the user interface unit 113, the grid switching unit 105 selects a grid having a grid frequency corresponding to the changed read pixel pitch.

As described above, according to this embodiment, when fluoroscopy or radiography is to be executed by using a single semiconductor sensor (FPD), a suitable grid is automatically selected in correspondence with a change in X-ray condition or the read pixel pitch of the sensor. The selected suitable grid is automatically inserted between the object 101 and the two-dimensional detector 106 so that fluoroscopy and radiography can be executed under optimum imaging conditions.

It is conventionally difficult to use a single semiconductor sensor for both fluoroscopy and radiography because of the small dose in fluoroscopy. In this embodiment, the operation can be implemented by, in fluoroscopy, making the pixel pitch large to increase the S/N ratio of an image and selecting a grid with a low grid ratio and low frequency to increase the grid transmission dose. In addition, when a stationary grid system is used to simplify the mechanism of the system at this time, optimum grid stripe reduction processing parameters are set in accordance with the grid to be used, thereby obtaining an image less affected by grid stripes.

<Second Embodiment>

Figure 6:
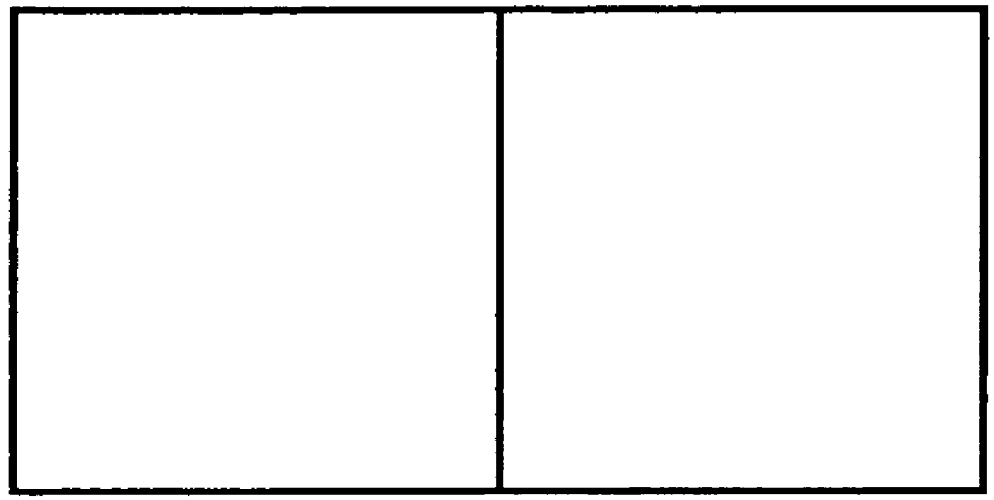
FIG. 6 is a view for explaining grid switching by a grid switching unit according to the second embodiment of the present invention.
Figure 7:
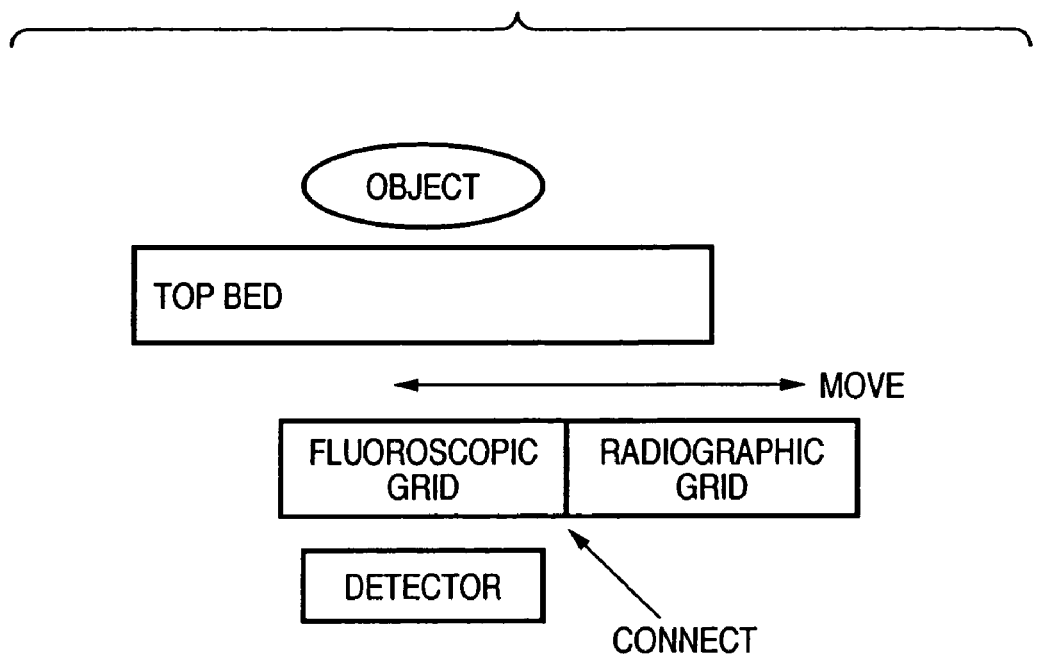
FIG. 7 is a system block diagram for explaining a grid switching state by the grid switching unit according to the second embodiment of the present invention.

FIG. 6 is a view for explaining grid switching by a grid switching unit according to the second embodiment of the present invention. FIG. 7 is a system block diagram for explaining a grid switching state by the grid switching unit according to the second embodiment of the present invention. The arrangement and operation of a radiographic system according to the second embodiment are basically the same as those of the above-described first embodiment. The second embodiment is different from the first embodiment in that the fluoroscopic grid and radiographic grid are connected in the same plane, as shown in FIGS. 6 and 7. Hence, the grid switching unit of this embodiment shifts the radiographic and fluoroscopic grids in correspondence with switching of the data acquisition mode, thereby changing the grid characteristic.

More specifically, as a characteristic feature of the radiographic system according to this embodiment, the fluoroscopic grid and radiographic grid are connected in the same plane, and the grid switching unit switches the grid by shifting the fluoroscopic grid and radiographic grid. Accordingly, for the fluoroscopic grid and radiographic grid connected in the same plane, when one grid is inserted, the other grid is automatically retracted.

As an advantage of this embodiment, since the grid is switched in fluoroscopy and radiography by shifting it, the structure is simplified, as compared to the first embodiment. In addition, space saving and high-speed switching can be implemented. The switching time from fluoroscopy to radiography can also be shortened. Furthermore, this embodiment is advantageous not only for a stationary grid but also for a grid that is to be reciprocated.

<Third Embodiment>

In the above-described first and second embodiments, the data acquisition modes are classified from the viewpoint of fluoroscopy and radiography. Instead, the system may be controlled depending on the pixel pitch in the data acquisition mode. More specifically, when the pixel pitch is decided by operator's selection using the user interface unit, an appropriate grid (i.e., the grid frequency) is decided in consideration of grid stripe reduction processing, as described above. In this way, a mechanism which selects and changes the grid in accordance with a change in acquisition pixel pitch can also be implemented.

More specifically, as a characteristic feature of the radiographic system according to this embodiment, the system comprises an X-ray unit which irradiates an object with X-rays, a two-dimensional detector which detects, through a grid, the X-rays which have passed through the object, and an image read control unit which acquires an image of the object from the detected X-rays, and further comprises a user interface which sets a data acquisition mode, a grid switching unit which selects a grid based on the data acquisition mode, and a grid stripe reduction unit which reduces grid stripes generated on the image by the grid. As a characteristic feature of the radiographic system, a pixel pitch in acquiring the image of the object from the X-rays detected by the two-dimensional detector is set by the user interface, and the grid switching unit selects a grid having a grid frequency which reduces the grid stripes on the image acquired at the set pixel pitch.

Note that the present invention can be applied to an apparatus comprising a single device or to system constituted by a plurality of devices.

Furthermore, the invention can be implemented by supplying a software program, which implements the functions of the foregoing embodiments, directly or indirectly to a system or apparatus, reading the supplied program code with a computer of the system or apparatus, and then executing the program code. In this case, so long as the system or apparatus has the functions of the program, the mode of implementation need not rely upon a program.

Accordingly, since the functions of the present invention are implemented by computer, the program code installed in the computer also implements the present invention. In other words, the claims of the present invention also cover a computer program for the purpose of implementing the functions of the present invention.

In this case, so long as the system or apparatus has the functions of the program, the program may be executed in any form, such as an object code, a program executed by an interpreter, or scrip data supplied to an operating system.

Example of storage media that can be used for supplying the program are a floppy disk, a hard disk, an optical disk, a magneto-optical disk, a CD-ROM, a CD-R, a CD-RW, a magnetic tape, a non-volatile type memory card, a ROM, and a DVD (DVD-ROM and a DVD-R).

As for the method of supplying the program, a client computer can be connected to a website on the Internet using a browser of the client computer, and the computer program of the present invention or an automatically-installable compressed file of the program can be downloaded to a recording medium such as a hard disk. Further, the program of the present invention can be supplied by dividing the program code constituting the program into a plurality of files and downloading the files from different websites. In other words, a WWW (World Wide Web) server that downloads, to multiple users, the program files that implement the functions of the present invention by computer is also covered by the claims of the present invention.

It is also possible to encrypt and store the program of the present invention on a storage medium such as a CD-ROM, distribute the storage medium to users, allow users who meet certain requirements to download decryption key information from a website via the Internet, and allow these users to decrypt the encrypted program by using the key information, whereby the program is installed in the user computer.

Besides the cases where the aforementioned functions according to the embodiments are implemented by executing the read program by computer, an operating system or the like running on the computer may perform all or a part of the actual processing so that the functions of the foregoing embodiments can be implemented by this processing.

Furthermore, after the program read from the storage medium is written to a function expansion board inserted into the computer or to a memory provided in a function expansion unit connected to the computer, a CPU or the like mounted on the function expansion board or function expansion unit performs all or a part of the actual processing so that the functions of the foregoing embodiments can be implemented by this processing.

As described above, according to the present invention, a grid in radiography or fluoroscopy can suitably be set, and fluoroscopy and radiography of an object can be executed under optimum imaging conditions.

The present invention is not limited to the above embodiments and various changes and modifications can be made within the spirit and scope of the present invention. Therefore, to apprise the public of the scope of the present invention, the following claims are made.

What is claimed is:

1. A radiographic apparatus comprising:
    mode selection means for selecting either a first mode for imaging a still image or a second mode for imaging a moving image;
    a plurality of grids for removing scattered radiation from radiation which has passed through an object;
    grid selection means for selecting one of the plurality of grids in accordance with the selected mode;
    a two-dimensional detector for converting the radiation from which the scattered radiation has been removed by the selected grid into electrical signals;
    setting means for setting a read condition on a basis of the selected mode, which includes read pixel pitch and an amplification degree;
    acquisition means for acquiring an image of the object from the electrical signals on a basis of the read condition set by the setting means; and
    grid stripe reduction means for reducing grid stripes on the image on a basis of parameters corresponding to the read pixel pitch; wherein in the read condition, the read pixel pitch of the two-dimensional detector and the amplification degree of the second mode are larger than in the first mode.

2. The apparatus according to claim 1, wherein a grid for the second mode and a grid for the first mode are connected in the same plane, and said grid selection means switches one of the grid for the second mode and the grid for the first mode by shifting the grid for the second mode and the grid for the first mode.

3. The apparatus according to claim 2, wherein the grid for the second mode and the grid for the first mode have different grid ratios or different grid frequencies.

4. The apparatus according to claim 1, further comprising irradiation means for irradiating the object with radiation, wherein
    tube voltage of the irradiation means in the case of the second mode is lower than that in the case of the first mode.

5. The apparatus according to claim 1, further comprising irradiation means for irradiating the object with radiation, wherein
    tube current of the radiation means in the case of the second mode is smaller than that in the case of the first mode.

6. A radiographic method comprising:
    a mode selection step for selecting either a first mode for imaging related to a still image or a second mode for imaging related to a moving image;
    an irradiation step of irradiating an object with radiation;
    a removing step of removing scattered radiation from radiation which has passed through the object;
    a grid selection step for selecting one of a plurality of grids in accordance with the selected mode;
    a two-dimensional converting step for converting the radiation from which the scattered radiation has been removed by the selected grid into electrical signals;
    a setting step for setting a read condition on a basis of the selected mode selected in said mode selection step, which includes read pixel pitch and an amplification degree;
    an acquisition step of acquiring an image of the object from the electrical signals on a basis of the read condition set in the setting step for setting a read condition;
    a setting step of setting imaging conditions; and
    a grid stripe reduction step of reducing grid stripes on the image on a basis of parameters corresponding to read pixel pitch, wherein in the setting step for setting the read condition, the read pixel pitch and the amplification degree of the second mode are larger than in the first mode.

7. A computer-readable medium encoded with a computer program which causes a computer to execute:
    a mode selection step for selecting either a first mode for imaging related to a still image or a second mode for imaging related to a moving image;
    an irradiation step of irradiating an object with radiation;
    a removing step of removing scattered radiation from radiation which has passed through the object;
    a grid selection step for selecting one of a plurality of grids in accordance with the selected mode;
    a two-dimensional converting step for converting the radiation from which the scattered radiation has been removed by the selected grid into electrical signals;
    a setting step for setting a read condition on a basis of the selected mode selected in said mode selection step, which includes read pixel pitch and an amplification degree;
    an acquisition step of acquiring an image of the object from the electrical signals on a basis of the read condition set in the setting step for setting a read condition;
    a setting step of setting imaging conditions; and
    a grid stripe reduction step of reducing grid stripes on the image on a basis of parameters corresponding to read pixel pitch,
wherein in the setting step for setting the read condition, the read pixel pitch and the amplification degree of the second mode are larger than in the first mode.

* * * * *